(12) United States Patent
Jennings

(10) Patent No.: US 8,293,350 B2
(45) Date of Patent: Oct. 23, 2012

(54) METHOD AND APPARATUS FOR A MOLD BARRIER

(75) Inventor: Jarrell L. Jennings, Schertz, TX (US)

(73) Assignee: Lancer Partnership, Ltd, San Antonio, TX (US)

( * ) Notice: Subject to any disclaimer, the term of this patent is extended or adjusted under 35 U.S.C. 154(b) by 92 days.

(21) Appl. No.: 12/286,823

(22) Filed: Oct. 2, 2008

(65) Prior Publication Data

US 2009/0065530 A1   Mar. 12, 2009

Related U.S. Application Data

(63) Continuation of application No. 11/176,858, filed on Jul. 7, 2005, now abandoned.

(51) Int. Cl.
*B67D 1/16* (2006.01)

(52) U.S. Cl. ....... 428/36.5; 222/108; 222/148; 222/173; 222/183; 222/630; 222/423; 222/403

(58) Field of Classification Search .................. 222/108, 222/148, 173, 183, 185, 630, 423, 403; 428/36.5
See application file for complete search history.

(56) References Cited

U.S. PATENT DOCUMENTS

| | | | | |
|---|---|---|---|---|
| 1,329,601 A * | 2/1920 | Hinsdale | .......................... | 239/29 |
| 2,761,288 A * | 9/1956 | Anderson et al. | ............. | 222/108 |
| 4,008,351 A * | 2/1977 | Inoue et al. | ................. | 428/411.1 |
| 4,048,274 A * | 9/1977 | Hoge et al. | .................... | 264/46.5 |
| 4,499,894 A * | 2/1985 | Buckley | .......................... | 126/707 |
| 4,592,490 A * | 6/1986 | McMichael | ................ | 222/129.1 |
| 4,944,335 A * | 7/1990 | Stembridge et al. | ............ | 141/95 |
| 5,221,016 A * | 6/1993 | Karpal | .......................... | 215/12.2 |
| 5,249,710 A * | 10/1993 | Hassell et al. | ............. | 222/146.6 |
| 5,333,759 A * | 8/1994 | Deering | ..................... | 222/129.1 |
| 5,335,819 A * | 8/1994 | Martin | ........................ | 222/146.6 |
| 5,350,085 A * | 9/1994 | Kidd et al. | ................. | 222/146.6 |
| 5,392,960 A * | 2/1995 | Kendt et al. | ................ | 222/129.1 |
| 5,397,032 A * | 3/1995 | Landers | ..................... | 222/146.6 |
| 5,418,055 A * | 5/1995 | Chen et al. | .................. | 428/317.7 |
| 5,486,407 A * | 1/1996 | Noell et al. | ................... | 428/215 |
| 5,490,614 A * | 2/1996 | Sardynski | .................. | 222/129.1 |
| 5,492,250 A * | 2/1996 | Sardynski | ..................... | 222/108 |
| 5,554,688 A * | 9/1996 | Yashima et al. | ................ | 525/71 |
| 5,585,407 A * | 12/1996 | Patel et al. | .................. | 514/772.6 |
| 5,614,568 A * | 3/1997 | Mawatari et al. | ............. | 523/122 |
| 5,669,528 A * | 9/1997 | Romero et al. | .................. | 222/53 |
| 6,209,184 B1 * | 4/2001 | Copeland et al. | ............... | 29/428 |
| 6,360,556 B1 * | 3/2002 | Gagliano | ......................... | 62/396 |
| 6,632,855 B1 * | 10/2003 | Beverly et al. | ................ | 523/122 |

(Continued)

FOREIGN PATENT DOCUMENTS

JP       2001-287797       10/2001

*Primary Examiner* — Michele L Jacobson
(74) *Attorney, Agent, or Firm* — Christopher L. Makay

(57) ABSTRACT

A mold barrier eliminates the establishment and continued resurgence of microbial colonies on product dispenser components routinely exposed to fluids and food products. The mold barrier may be utilized in a product dispenser to prevent the establishment of mold colonies on the product dispenser. The mold barrier adheres to potentially exposed surfaces to create an impenetrable boundary layer, thereby preventing the errant product from permeating into porous materials not suitable for product contact. Upon contacting the mold barrier, the errant product moves downward. Residues left from the errant product may be removed when the product dispenser and mold barrier are sanitized during routine cleansing operations. Upon sanitization, the product dispenser may be restored to a sanitized condition.

17 Claims, 5 Drawing Sheets

U.S. PATENT DOCUMENTS

| | | | |
|---|---|---|---|
| 6,698,229 B2 * | 3/2004 | Renken et al. | 62/390 |
| 6,840,407 B2 * | 1/2005 | Lassota et al. | 222/183 |
| 6,880,358 B2 * | 4/2005 | Lucas et al. | 62/344 |
| 7,287,671 B2 * | 10/2007 | Morrow et al. | 222/129.1 |
| 2003/0034360 A1 * | 2/2003 | Lassota et al. | 222/185.1 |
| 2003/0071076 A1 * | 4/2003 | Tenzer et al. | 222/385 |
| 2003/0089423 A1 * | 5/2003 | Barton et al. | 141/198 |
| 2003/0102330 A1 * | 6/2003 | Cote | 222/129.1 |
| 2004/0031810 A1 * | 2/2004 | Thompson | 221/226 |
| 2004/0168466 A1 * | 9/2004 | Landers et al. | 62/390 |
| 2005/0042247 A1 * | 2/2005 | Gomoll et al. | 424/412 |
| 2005/0087572 A1 * | 4/2005 | Hirota et al. | 222/630 |
| 2005/0154361 A1 * | 7/2005 | Sabesan | 604/365 |
| 2006/0111513 A1 * | 5/2006 | Slansky et al. | 525/178 |

* cited by examiner

METHOD AND APPARATUS FOR A MOLD BARRIER

CROSS-REFERENCE TO RELATED APPLICATION

This application is a continuation of patent application Ser. No. 11/176,858, which was filed Jul. 7, 2005 now abandoned.

BACKGROUND OF THE INVENTION

1. Field of the Invention

The present invention relates to food product dispensing equipment and, more particularly, but not by way of limitation, to methods and an apparatus for creating a mold barrier in a food product dispenser.

2. Description of the Related Art

In the food product dispensing industry, product dispensers must conform to stringent design criteria to receive approval for public use from the National Sanitation Foundation. While National Sanitation Foundation approval does not guarantee the elimination of cleanliness problems, it does minimize the possibility of cleanliness issues. National Sanitation Foundation design criteria addresses all food contact components, as well as a food product dispensing area known as a "splash zone." However, components disposed beneath or beyond the surfaces of the "splash zone" may prove to be problematic at a later time.

The "splash zone" may include components that are removable for sanitizing purposes. While that solves the problems of sanitizing the "splash zone" components, it does not address items disposed beneath or behind the "splash zone" components. While a splash plate may serve as an effective means for containing sprays and spills, it is not fully effective. For instance, in drop-in ice cooled dispensing equipment, an area behind a splash plate often is routinely exposed to over sprays, spills, splashes, and the like. While the exposed portions of product dispensers are routinely sanitized, those components located behind the exposed portions may be hard to reach or are composed of materials not conducive to cleansing or sanitizing, and therefore may create future problems.

As product dispensers are typically in the field for years, small cleansing issues normally out of view may fester for extended periods without proper attention. Illustratively, a foamed portion of a tower located directly behind a splash plate may be doused often with either a concentrate or a diluent or both. If untreated, the area may develop mold in the exposed area. Mold on any food product dispenser may be unsightly, cause a health risk, or if left untended, the mold may spread and ultimately force the condemnation of the product dispenser.

Accordingly, a method and apparatus that eliminates the characteristics conducive to the establishment and continued propagation of a mold colony in a product dispenser would be beneficial to consumers, dispenser operators, food product producers, as well as the manufacturers of the food product dispensers.

SUMMARY OF THE INVENTION

In accordance with the present invention, a method and apparatus for a mold barrier eliminates the establishment and continued resurgence of microbial colonies on product dispenser components routinely exposed to fluids or food products. The mold barrier provides an impenetrable barrier to fluids that may normally come into contact with permeable components, thereby preventing permeation of permeable components. The mold barrier may then be sanitized to restore the mold barrier, the product dispenser component, and the product dispenser on which the mold barrier is installed to a sanitized condition.

The mold barrier adheres to potentially exposed surfaces to create an impenetrable boundary layer, thereby preventing the errant product from permeating into porous materials not suitable for product contact. Upon contacting the mold barrier, the errant product moves downward. Residues left from the errant product may be removed when the product dispenser and mold barrier are sanitized during routine cleansing operations. Upon sanitization of the mold barrier surfaces, the product dispenser may be restored to a sanitized condition.

It is therefore an object of the present invention to provide a mold barrier for use on product dispenser components containing porous surfaces.

It is a further object of the present invention to provide a product dispenser including a mold barrier.

It is still further an object of the present invention to provide a method for eliminating the establishment and continued propagation of microbial colonies in a product dispenser.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

DETAILED DESCRIPTION OF THE PREFERRED EMBODIMENT

Figure 1A:
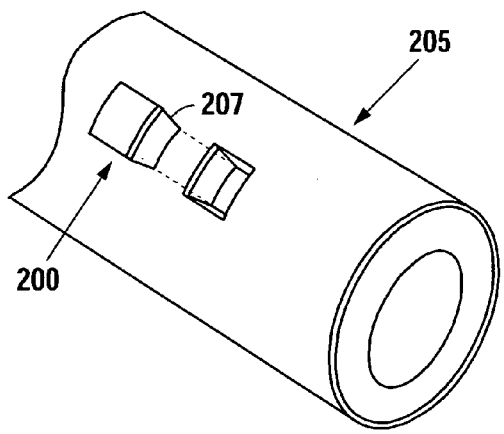
FIG. 1a provides a detail view of a product dispenser component cross section according to the subject invention.

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

In a simplest form, a mold barrier 200 encapsulates porous components that may be utilized in a product dispenser, and may be potentially or temporarily exposed to environments or products that may contain bacteria or may serve as a platform for the establishment of a mold colony. The mold barrier 200 provides a sanitizable surface, thereby restoring the product dispenser components to a sanitized condition. As shown in FIGS. 1a-1d, a section 207 of a product dispenser component 205 includes an exposed surface 206, section surfaces 208, and the mold barrier 200. The mold barrier 200 may include an inner face 201, an outer face 202, and section surfaces 209. The product dispenser component 205 may be any type of component containing a porous surface as required by a product dispenser, including tubing, insulation, woven components, electrical harnesses, foam inserts, elastomeric seals, and the like. Product dispenser components 205 containing porous exposed surfaces are susceptible to permeation by fluids and malleable solutions including pastes and gels. Examples of fluids and pastes that may penetrate the porous surfaces include beverages and food products. Examples of material types for the various components may include fabrics, insulations, foams, elastomeric sealing components, wood cabinetry, and wood pulp based products.

The mold barrier 200 is an impervious liner, and may be constructed from virtually any material of a nonporous nature that is resistant to common sanitization chemicals, polystyrene or ABS (acrylonitrile butadiene styrene), for example. Preferably, the mold barrier 200 is of a thin construction to minimize impact on an apparatus outside of its intended purpose. The mold barrier 200 may be flexible to conform to an irregular surface, or the mold barrier 200 may be applied as a spray that adheres to an exposed surface 206 of the product dispenser component 205 and forms a solid nonporous protective coating similar to a spray paint. The mold barrier 200 may further be constructed from other resins, metals, curing gelatins, pastes, ceramics, glass, and the like.

Figure 1B:
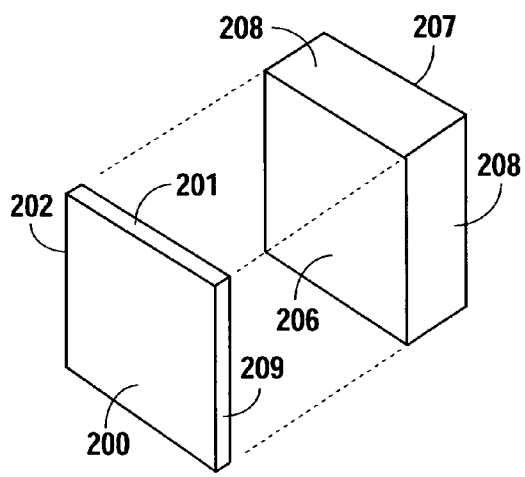
FIG. 1b provides an exploded view of the product dispenser component constituents according to the invention.
Figure 1C:
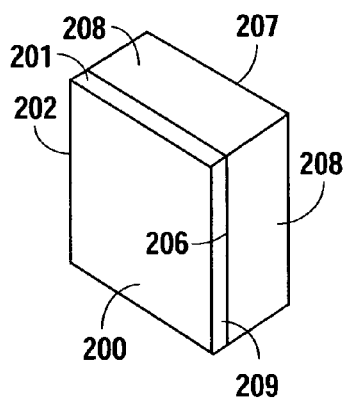
FIG. 1c provides a perspective view illustrating the relationship between the mold barrier and an exposed surface of the product dispenser component according to the invention.

As shown in FIG. 1b, the inner face 201 of the mold barrier 200 is placed adjacent to the exposed surface 206 of the component to encapsulate the exposed surface 206. It should be clear to one of ordinary skill in the art that the relationship between the exposed surface 206 and the inner surface 201 of the mold barrier 200 is representative of the complementary surfaces of the product dispenser component 205 and the mold barrier 200 disposed about the product dispenser component 205. The mold barrier 200 may be restrained in place utilizing mechanical restraints or the mold barrier 200 may be applied to the exposed surface 206 to form a curing film, thereby adhering to the exposed surface 206. One of ordinary skill in the art will further recognize that product dispenser components 205 formed in place may be utilized to adhere to a preformed mold barrier 200. Illustratively, a two-part foam may be shot into a foaming fixture containing a mold barrier 200. During curing, the foam permanently adheres to components contacting the foam, including the mold barrier 200.

In use, the mold barrier 200 is placed adjacent to the exposed surface 206 of the product dispenser component 205, such that the inner surface 201 of the mold barrier 200 is adjacent to and encapsulates the exposed surface 206 of the product dispenser component 205. In this position, the exposed surface 206 of the product dispenser component 205 is protected from contact with fluids, errant product, weather factors, and airborne microorganisms. The impervious construction of the mold barrier 200 prevents fluids from penetrating the mold barrier 200 to reach the exposed surface 206 of the section 207, as well as the product dispenser component 205. The elimination of the porous exposed surface 206 being exposed to fluids prevents the saturation of the porous exposed surface 206 with organic fluids, product, or contaminated fluids, as well as any associated residues that remain after the porous exposed surface 206 dries. Fluids or products coming into contact with the mold barrier 200 remain on the outer surface 202 of the mold barrier 200 or move downward due to gravitational forces. Any residues remaining on the outer surface 202 may be removed and neutralized by wiping the outer surfaces 202 of the mold barrier 200 with a sanitizing solution, thereby restoring the product dispenser component 205 to a sanitized condition.

Figure 1D:
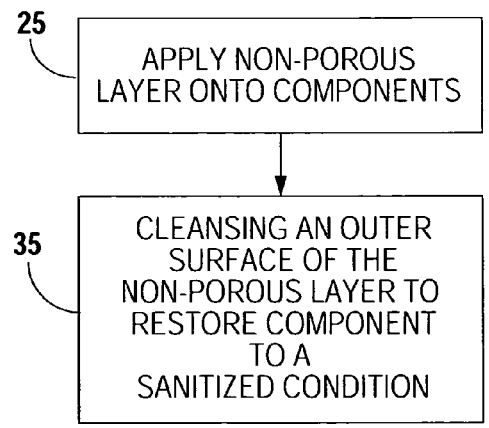
FIG. 1d provides a flowchart illustrating the method steps for creating a mold barrier according to the invention.

FIG. 1d provides a flowchart illustrating the method steps associated with utilizing a mold barrier 200. The process commences with step 25, wherein a mold barrier 200 is placed adjacent to an exposed surface 206 of a product dispenser component 205, such that an inner surface 201 of the mold barrier 200 encapsulates the exposed surface 206 of the product dispenser component 205. Once in position, errant fluids or products may contact the outer surface 202 of the mold barrier 200 in lieu of contacting the exposed surface 206 of the product dispenser component 205. As the mold barrier 200 is impervious, the fluids or product remain on the outer surface 202 of the mold barrier 200. The process then continues with step 35, wherein the outer surface 202 of the mold barrier 200 is sanitized by cleansing with a sanitizing solution, thereby restoring the outer surface 202 of the mold barrier 200 and the product dispenser component 205 to a sanitized condition.

In an extension of this invention, a product dispenser 300 includes a housing 310, at least one product dispensing circuit 311, at least one product valve 312, and a mold barrier 320. The housing 310 may be any structure suitable for containing and supporting components of the beverage dispenser 300. Illustratively, the housing 310 may include a frame 314, and an insulation 315. The frame 314 may include an attachment means for the product valve 312 and the product dispensing circuit 311. The frame 314 may further support the insulation 315 such that the insulation 315 maintains temperatures of the product disposed within the housing 310. Illustratively, the insulation 315 may be disposed around the outsides of the housing 310 or around components of the product dispensing circuit 311.

In this extension of the invention, the product dispensing circuit 311 is in communication with the product valve 312 and a product supply 313, such that a product is delivered from the product supply 313 to the product valve 312. The term product dispenser in this extension of the invention is defined to include dispensers of virtually all types of products including beverages and food product dispensers. Illustratively, examples of product types may include carbonated drinks, ambient drinks, juices, milks, teas, soups, condiments, sauces, flavored waters, and the like. The products may further require a diluent, in which case the product dispenser 300 could further include a diluent dispensing circuit 316 connectable to a diluent supply 317.

The mold barrier 320 is an impervious layer located adjacent to exposed porous surfaces on or about the housing 310, thereby encapsulating the porous exposed surfaces of the insulation 315, insulated product lines, electrical harnesses, and the like. In the installed position, the mold barrier 320 provides an impermeable layer around the surfaces of the insulation 315 that may become exposed to spills, sprays, or drops of a dispensed product. Illustratively, the areas located beneath the product dispensing valve 312 run a substantial risk of becoming exposed to errant product. In this extension of the invention, the mold barrier 320 may be a preformed component that may be secured to the insulation 315 using a variety of methods, or a sprayed on component. One of ordinary skill in the art will recognize that the mold barrier 320 may be flexible to complement the shape of product dispenser 300 components.

In use, the product dispenser 300 receives a dispense command and delivers a product or a diluent or both to the product dispensing valves 312 for mixing and delivery into an operator's cup. During the execution of the dispense command, exposed faces of the product dispenser 300 may be exposed to over sprays, drips, and spills. The errant product lands on the mold barrier 320, is unable to penetrate the mold barrier 320, and is forced to move downward. As the errant product is unable to soak through the mold barrier 320, the errant product will remain on the outer surfaces of the mold barrier 32, and may be removed at a later time by an operator using a normal cleansing process. Illustratively, the operator may wipe the outer surface of the mold barrier 320 with a sponge soaked in a readily available sanitizing solution, thereby restoring the product dispenser 300 to a sanitized condition.

Figure 2A:
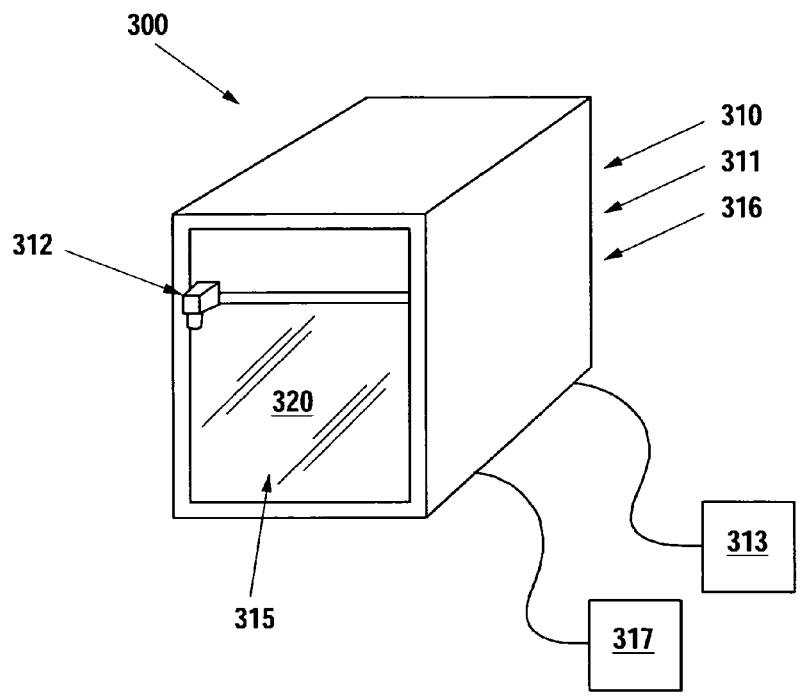
FIG. 2a provides a perspective view of a product dispenser utilizing a mold barrier according to the invention.
Figure 2B:
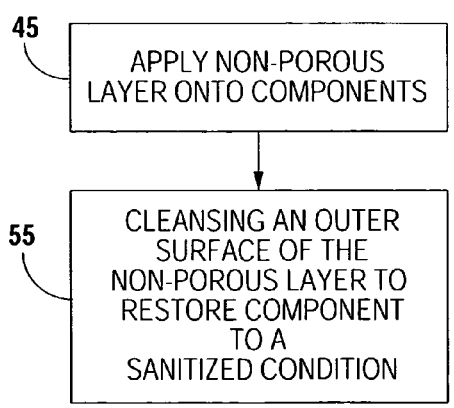
FIG. 2b provides a flowchart illustrating the method steps for creating a mold barrier according to the invention.
Figure 3:
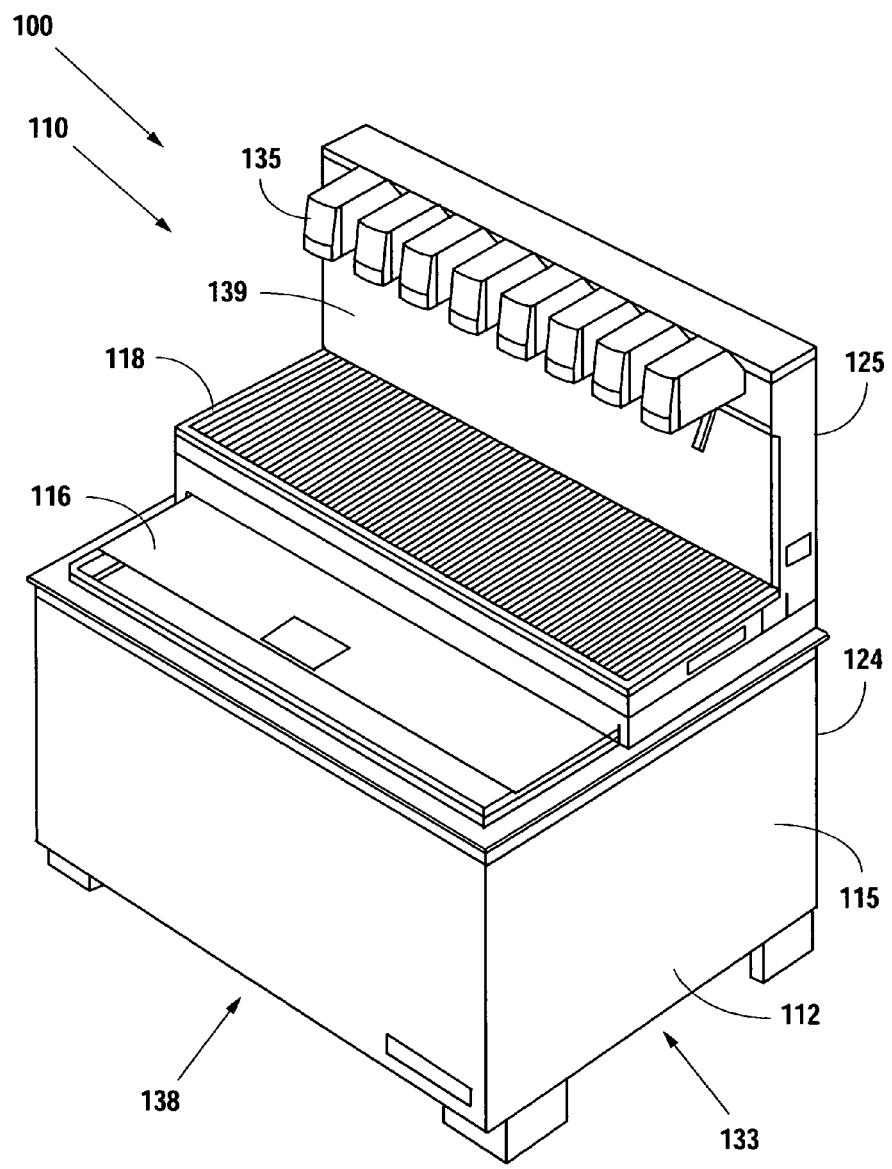
FIG. 3 provides a perspective view of a tower dispenser according to an illustrated example of the invention.
Figure 4:
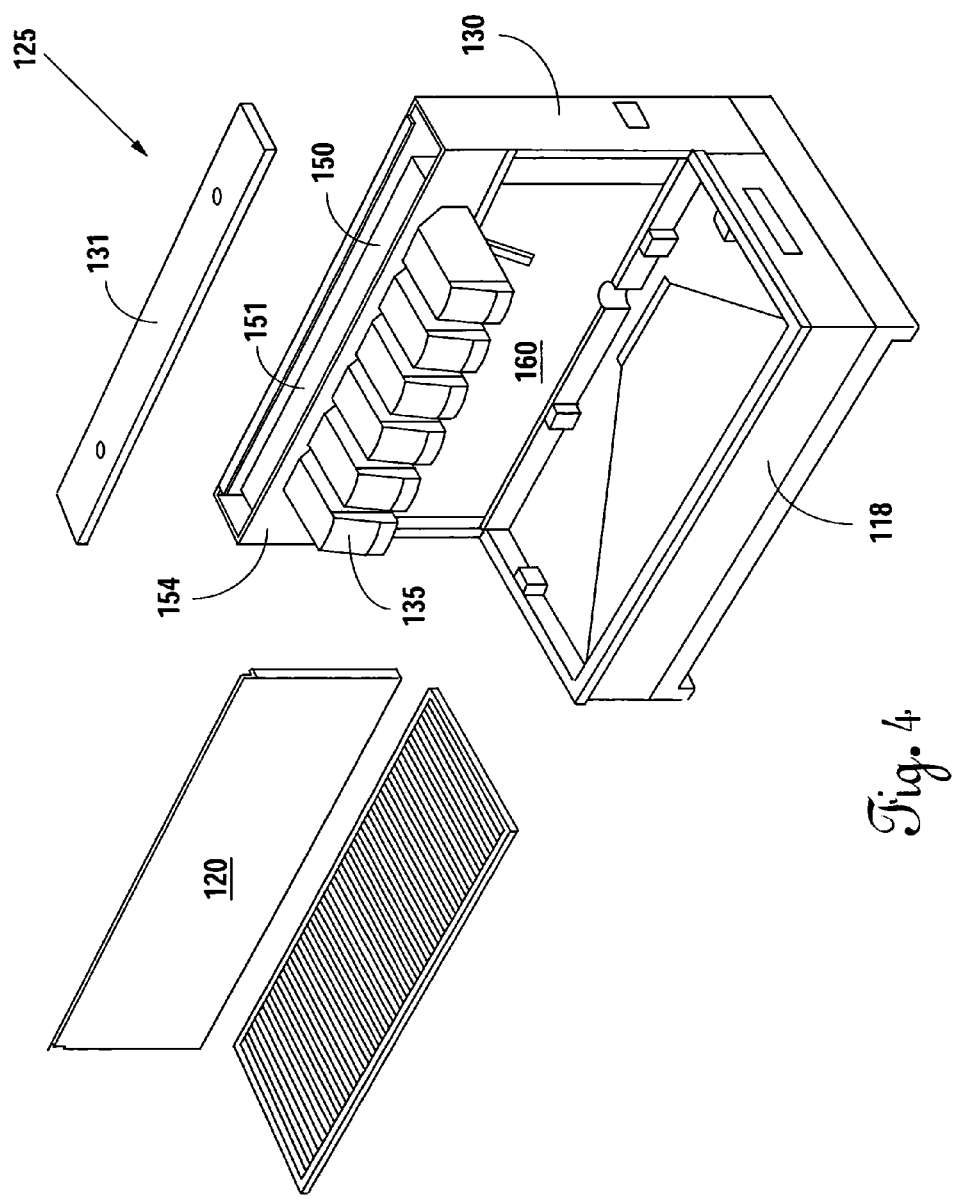
FIG. 4 provides a detail view of a tower portion including a mold barrier according to the illustrated example.
Figure 5:
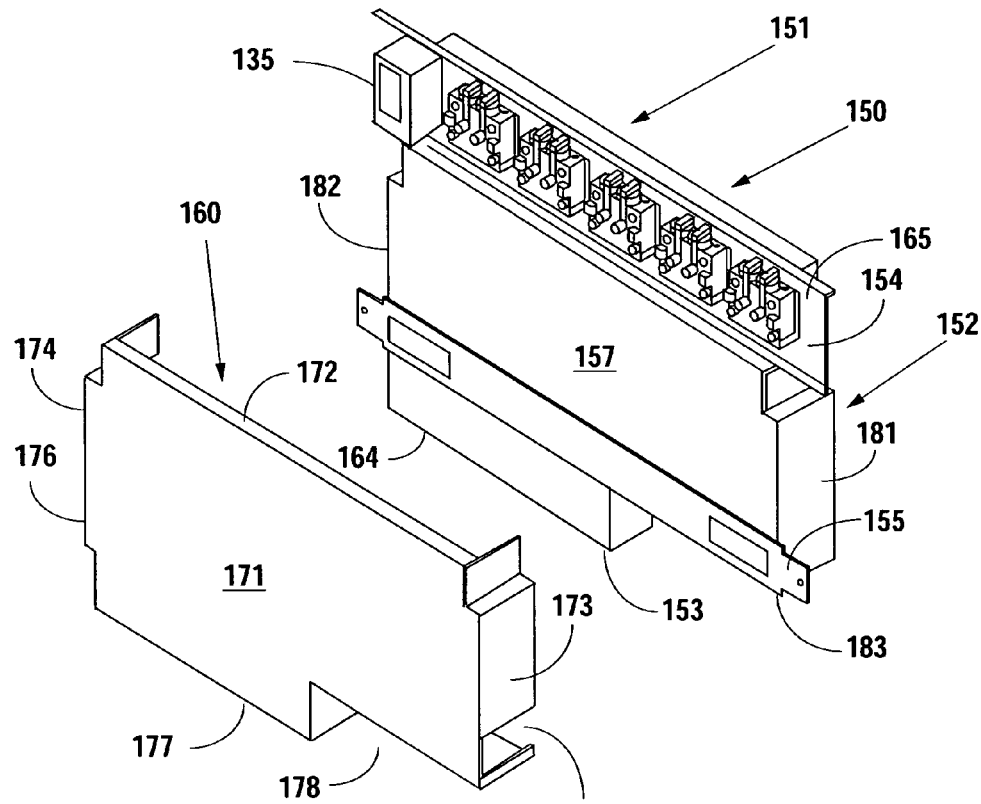
FIG. 5 provides an exploded view of a tower portion according to the illustrated example.

FIG. 2b provides a method flowchart illustrating the method steps for eliminating surfaces conducive to the establishment of a microbial colony. The process commences with step 45, wherein an impenetrable barrier is created on outside surfaces of potentially exposed components that include penetrable surfaces. The process continues with step 55, wherein outer surfaces of the impenetrable barrier are sanitized to exterminate any microbial growth, thereby eliminating the continued propagation of microbial colonies on the impenetrable and the penetrable surfaces.

While this mold barrier 320 has been disclosed as a thin layer about the product dispenser 300 components, one of ordinary skill in the art will recognize that the mold barrier 320 may be formed from other types of construction, including plastic wraps, shrink wrap, and anti-microbial materials. One of ordinary skill in the art will further recognize that the method of application and the thickness of the mold barrier 320 may vary with the form of construction. Illustratively, the mold barrier 320 could be brushed on or sprayed on either before or after assembly to create an impenetrable surface. Still further, the mold barrier 320 could be a preformed component suitably restrained to provide coverage to exposed porous surfaces, or even a preformed component adhered to the exposed porous surfaces.

An illustrative example of a mold barrier application in a product dispenser is shown in FIGS. 3-8, wherein a product dispenser 100 includes a housing 110 having a lower portion 124, and a tower assembly 125. The product dispenser 100 may be designed to suspend from a counter, such that the tower assembly 125 protrudes from a counter top. The lower portion 124 may include a storage chamber 115 for storing ice until use, and may further include a cold plate 112 that serves as a floor of the storage chamber 115, such that the cold plate 112 is cooled by the ice stored within the storage chamber 115. Access to the storage chamber 115 is gained through an access port 116 of the storage chamber 115.

The lower portion 124 may still further include fluid flow paths 133 containing inlets 138 and outlets 139 connectable to a product source and a diluent source for the delivery of a diluent and a concentrate to the outlets 139 and the tower assembly 125. In this illustrative example, the outlets 139 are disposed at an upper end of the lower portion 124, such that they are accessible from the top. The concentrate and diluent flow paths may be conditioned by the cold plate 112, and may include flow metering and control devices commonly utilized in a product dispenser for the regulation of fluids disposed within the flow paths. The housing 110 may further include a drip tray 118 that collects spills, sprays, and drips from dispensing operations. The drip tray 118 may further close out the storage chamber 115 to protect and insulate the ice.

The tower assembly 125 includes a tower head assembly 150, a shroud 130, a shroud cap 131, and a splash plate 120. The tower head assembly 150 includes a tower head 151 and product dispensing valves 135. The tower head 151 may include product and diluent flow paths 153, an insulation 152, a mold barrier 160, a face plate 154, and a pry bracket 155. In this illustrative example, the product and diluent flow paths 153 include inlets 164 for communicating with the outlets 139 of the product and diluent flow paths 133 of the lower portion 124 and outlets 165 for communicating with the inlets of the product dispensing valves 135.

The shroud 130 is of a sheet metal construction, preferably stainless steel to meet cleanability requirements. The shroud 130 is adaptable to the lower portion 124 and the face plate 154 to surround and protect the tower head 151. The shroud cap 131 is also constructed from stainless steel, and is utilized to close out a top of the tower head assembly 150. The splash plate 120 is similarly constructed from stainless steel to meet cleanability requirements. The splash plate 120 is removable, and is used to close out the portion of the tower assembly 125 disposed beneath the product dispensing valves 135.

The insulation 152 is of a closed cell construction, preferably a two part urethane. The insulation 152 surrounds the product and diluent flow paths 153, thereby insulating the product and diluent flow paths 153. In this detailed example, the insulation 152 is formed in a foaming fixture to simplify the insertion of the insulation 152 around the product and diluent flow paths 153.

The mold barrier 160 is disposed around the insulation 152 to provide an impermeable layer around the surfaces of the insulation 152 that may become exposed to spills, sprays, or drops of a dispensed product. Illustratively, the areas located beneath the product dispensing valve 135 and behind the splash plate 120 run a substantial risk of becoming exposed to errant product. In this detailed example, the mold barrier 160 is a preformed thirty thousandths of an inch polystyrene sheet that may be secured to the insulation 152 using a variety of methods. The mold barrier 160 includes a planar face 171 having a first flange 173, a second flange 174, a third flange 172, and a fourth flange 178. The planar face 171 is complementary in shape to a front face 157 of the tower head 151. The flanges 172, 173, 174, and 178 extend in a direction towards the tower head 151, such that they are adjacent to a first side 181, a second side 182, and a third side 183 of the tower head 151. One of ordinary skill in the art will recognize that the mold barrier 160 may include additional flanges or adjoining sides to further complement the shape of the tower head 151 or additional components. The mold barrier 160 further includes a first relief 175 in the first flange 173, a second relief 176 in the second flange 174, and a third relief 177 in the fourth flange 178. The first relief 173 and the second relief 174 allow the mold barrier 160 to pass over an installed pry bracket 155. The third relief 177 allows for the passage of the product and diluent flow paths 153 through to the lower portion 124. Illustratively, the mold barrier 160 may be placed into a foaming fixture that is filled with a curing foam, thereby permanently attaching the mold barrier 160 to the insulation 152, or the preformed sheet may be secured using adhesives, or mechanical fasteners.

The face plate 154 and the pry bracket 155 may be constructed from formed stainless steel, and may include apertures to accommodate the inlets 164 or outlets 165 of the product and diluent flow paths 153. The outlets 165 of the product and diluent flow paths 153 may pass through the apertures in the face plate 154 for alignment during foaming operations. The inlets 164 of the product and diluent flow paths 153 may pass through the apertures of the pry bracket 155 to gain access to the lower portion 124. The pry bracket 155 further includes attachment points for connection to the shroud 130.

Figure 6:
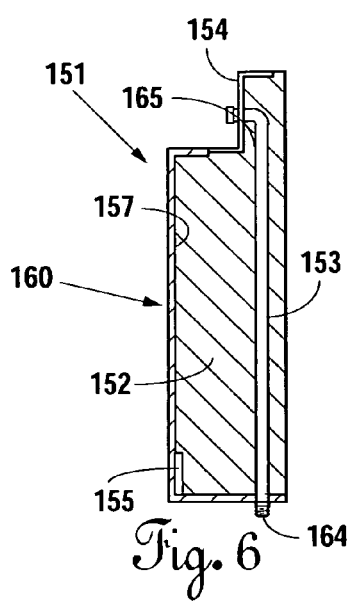
FIG. 6 provides a section view of a tower head containing a mold barrier according to the illustrated example.

In this illustrative example, the tower head 151 is assembled utilizing a foaming fixture. Assembly commences with the insertion of a mold barrier 160 into the foaming fixture. In a foaming position, the mold barrier 160 nests in the foaming fixture, and substantially lines the walls of the foaming fixture. Next, the product and diluent flow paths 153, the pry bracket 155 and the face plate 154 are oriented in the foaming fixture. The inlets 164 of the product and diluent flow paths 153 are positioned in the apertures of the pry bracket 155, such that they are in positions complementary to the outlets 139 of the fluid flow paths 133 disposed in the lower portion 124. The outlets 165 of the product and diluent lines 153 are then located in the apertures of the face plate 154, such that the locations of the outlets 165 are complementary to the spacing of the inlets of the product dispensing valves 135. The pry bracket 155 is then oriented in the first relief 175 and the second relief 176, such that the pry bracket 155 is fully inserted into the first relief 175 and the second relief 176. Once fully inserted, the foaming fixture may be closed, and a two part foam may be injected into the foaming cavity. Upon curing, the two part foam adheres to the face plate 154, the pry bracket 155, the product and diluent flow paths 153, and the mold barrier 160, and then hardens to form an integral tower head 151. Once cured, the product and diluent flow paths 153 and the mold barrier 160 in the tower head 151 are permanently located in position, and the tower head 151 may be installed or removed as a unit. As shown in FIG. 6, the mold barrier 160 lines the front face 157 of the tower head 151 and extends to adjacent faces, thereby sealing the potentially exposed surfaces of the tower head 151.

Upon further assembly, the tower head 151 is mounted to the lower portion 124 of the product dispenser 100 such that the outlets 139 of the lower portion 124 are coupled to the inlets 164 of the tower head 151. The product dispensing valves 135 may then be installed onto the face plate 154 of the tower head 151 such that the inlets of the product dispensing valves 135 are coupled to the outlets 165 of the product and diluent flow paths 153 of the tower head 151, thereby completing the product and diluent delivery circuits. The shroud 130 may then be installed to protect the tower head 151. The build continues with the installation of the shroud cap 131 onto the open portion of the shroud 130. The installation of the splash plate 120 follows, thereby fully encapsulating the tower head 151 behind the shroud 130, the cap 131, and the splash plate 120. As the splash plate 120 is removable for cleaning, the area directly behind the splash plate 120 may occasionally be exposed to splashes, drips, or sprays when the splash plate 120 is incorrectly installed or removed from the product dispenser 100.

In use, when the product dispenser 100 receives a dispense command, it delivers a product or a diluent or both to one of the product dispensing valves 135 for mixing and delivery into an operator's cup. In cases where the splash plate 120 is removed during the execution of a dispense command, exposed faces of the tower head 151 may be exposed to oversprays, drips, and the like. The errant product lands on the planar face 171 of the mold barrier 160 on the tower head 151, is unable to penetrate the mold barrier 160, and is forced to move downward. As the errant product is unable to soak into the mold barrier 160, the errant product may be removed at a later time by an operator using a normal cleansing process, illustratively, wiping the tower head 151 with a sponge soaked in a readily available sanitizing solution, thereby restoring the product dispenser 100 to a sanitized condition.

Figure 7:
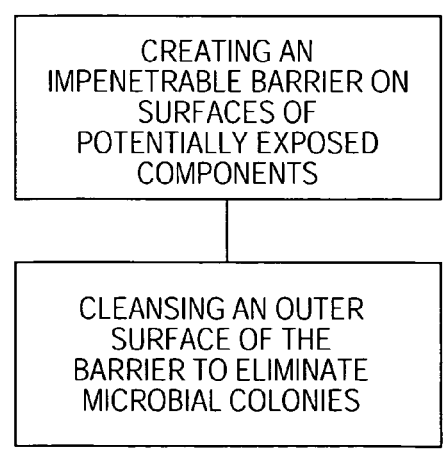
FIG. 7 provides a flowchart illustrating the method steps for restoring a product dispenser to a sanitized condition according to the illustrated example.

FIG. 7 provides a method flowchart illustrating the method steps for eliminating surfaces conducive to the establishment of a microbial colony. The process commences with step 10, wherein an impenetrable barrier is created on outside surfaces of potentially exposed components that include penetrable surfaces. The process continues with step 20, wherein outer surfaces of the impenetrable barrier are sanitized to exterminate any microbial colonies, thereby eliminating the continued propagation of microbial colonies on the impenetrable and the penetrable surfaces.

While this mold barrier 160 has been disclosed as a formed sheet of polystyrene that is foamed in place, one of ordinary skill in the art will recognize that the mold barrier 160 may be formed from other types of construction, including plastics, plastic wraps, shrink wrap, and anti-microbial materials. One of ordinary skill in the art will further recognize that the method of application and the thickness of the mold barrier 160 may vary with the form of construction. Illustratively, the mold barrier 160 could be brushed on or sprayed on either before or after the tower head 151 is foamed to create an impenetrable surface.

Although the present invention has been described in terms of the foregoing preferred embodiment, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

I claim:

1. A product dispenser adapted to dispense liquids and diluents therefrom, comprising:
   a housing;
   a product dispenser component disposed within the housing, the product dispenser component including a porous surface; and
   a layer impervious to liquids and diluents disposed between the porous surface of the product dispenser component and the housing, wherein liquids and diluents dispensed from the product dispenser that spill onto and then penetrate the housing contact the layer in lieu of the porous surface.

2. The product dispenser according to claim 1, wherein the layer is disposed on the product dispenser component.

3. The product dispenser according to claim 1, wherein the layer is formed integrally with the product dispenser component.

4. The product dispenser according to claim 1, wherein the product dispenser component comprises insulation.

5. The product dispenser according to claim 4, wherein the layer is disposed on the insulation.

6. The product dispenser according to claim 4, wherein the layer is formed integrally with the insulation.

7. The product dispenser according to claim 4, further comprising a product line at least partially surrounded by the insulation.

8. The product dispenser according to claim 7, wherein the housing comprises a tower head, further wherein the product line, the insulation, and the layer are disposed within the tower head.

9. The product dispenser according to claim 1, wherein the product dispenser component comprises a product line.

10. The product dispenser according to claim 4, wherein the insulation is a two-part urethane.

11. The product dispenser according to claim 4, wherein the insulation is foamed in place.

12. The product dispenser according to claim 1, wherein the layer impervious to liquids and diluents is formed from acrylonitrile butyl styrene.

13. The product dispenser according to claim 1, wherein the layer impervious to liquids and diluents is formed from polystyrene.

14. The product dispenser according to claim 1, wherein the layer impervious to liquids and diluents is formed from anti-microbial material.

15. The product dispenser according to claim 1, wherein the layer impervious to liquids and diluents is preformed and placed between the product dispenser component and the housing.

16. The product dispenser according to claim 1, wherein the layer impervious to liquids and diluents is applied onto the product dispenser component.

17. The product dispenser according to claim 1, wherein a foam is delivered into a foaming fixture containing the layer and the product dispenser component.

* * * * *